(12) United States Patent
Fisher et al.

(10) Patent No.: US 8,121,667 B2
(45) Date of Patent: Feb. 21, 2012

(54) INTERFACED BASE UNIT AND DISPLAY SYSTEM FOR AN MRI MAGNET ROOM

(75) Inventors: Stephen Douglas Fisher, Winter Springs, FL (US); Robert A. Harwell, Orlando, FL (US); Jorgen Kilden-Pedersen, Orlando, FL (US); Arthur R. Weeks, Jr., Oviedo, FL (US); Kenneth Van Arsdel, Orlando, FL (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 449 days.

(21) Appl. No.: 12/440,033

(22) PCT Filed: May 10, 2007

(86) PCT No.: PCT/US2007/068626
§ 371 (c)(1),
(2), (4) Date: Mar. 5, 2009

(87) PCT Pub. No.: WO2007/134144
PCT Pub. Date: Nov. 22, 2007

(65) Prior Publication Data
US 2010/0036236 A1    Feb. 11, 2010

Related U.S. Application Data

(60) Provisional application No. 60/799,884, filed on May 12, 2006.

(51) Int. Cl.
*A61B 5/05*    (2006.01)
(52) U.S. Cl. ......... 600/411; 600/300; 600/301; 600/410
(58) Field of Classification Search .......... 600/300–301, 600/363–365, 373–374, 377–379, 382–384, 600/386–394, 407–481, 485, 500–503, 509, 515–519, 529–531, 544–547, 549, 587–595; 439/620.01, 620.07, 620.21, 625, 626, 627; 361/114, 115, 600, 636, 640, 643, 679.01, 679.04, 679.05, 679.06, 679.4, 679.41, 816, 817, 818, 819
See application file for complete search history.

(56) References Cited

U.S. PATENT DOCUMENTS
4,249,813 A * 2/1981 Nihei ........................... 396/203
(Continued)

FOREIGN PATENT DOCUMENTS
EP       735499 A1 * 10/1996
(Continued)

OTHER PUBLICATIONS

Frese, G. et al "Magnetic Resonance Imaging (MRI) and Electromagnetic Fields (EMF)", Apr. 10th, 2003, p. 1-3.*
(Continued)

*Primary Examiner* — Sam Yao
*Assistant Examiner* — Marie Archer

(57) ABSTRACT

A base unit operable with a wireless patient monitoring unit used to acquire physiological data during an MRI examination is constructed to have a detachable display unit. The detachable display unit wirelessly communicates with the base unit when in a roving mode. The detachable display unit may also have a magnetically-hardened power supply that does not saturate during an MRI examination. Such a magnetically-hardened power supply allows the display unit to operate when proximate or in the magnetic field generated by an MRI machine during an MRI examination.

19 Claims, 3 Drawing Sheets

U.S. PATENT DOCUMENTS

| | | | |
|---|---|---|---|
| 4,662,276 A * | 5/1987 | Schrotz | 101/111 |
| 5,076,275 A * | 12/1991 | Bechor et al. | 600/410 |
| 5,184,074 A * | 2/1993 | Arakawa et al. | 324/309 |
| 5,394,873 A * | 3/1995 | Kraemer et al. | 600/523 |
| 5,464,014 A * | 11/1995 | Sugahara | 600/411 |
| 5,565,941 A * | 10/1996 | Kaneko | 396/177 |
| 5,600,108 A | 2/1997 | Newham | |
| 5,733,247 A * | 3/1998 | Fallon | 600/410 |
| 5,864,331 A * | 1/1999 | Anand et al. | 345/656 |
| 6,052,614 A * | 4/2000 | Morris et al. | 600/509 |
| 6,148,229 A * | 11/2000 | Morris et al. | 600/509 |
| 6,198,285 B1 * | 3/2001 | Kormos et al. | 324/318 |
| 6,246,573 B1 | 6/2001 | Khan et al. | |
| 6,400,155 B2 * | 6/2002 | Kormos et al. | 324/318 |
| 6,704,592 B1 * | 3/2004 | Reynolds et al. | 600/411 |
| 6,961,604 B1 * | 11/2005 | Vahasalo et al. | 600/410 |
| 7,123,009 B1 * | 10/2006 | Scott | 324/311 |
| 7,167,741 B2 * | 1/2007 | Torchia et al. | 600/427 |
| 7,221,159 B2 * | 5/2007 | Griffiths et al. | 324/318 |
| 7,276,661 B2 * | 10/2007 | Wegner et al. | 174/58 |
| 7,296,775 B2 * | 11/2007 | Mayer | 248/349.1 |
| 7,327,863 B1 * | 2/2008 | Green et al. | 382/128 |
| 7,391,214 B2 * | 6/2008 | Adachi | 324/318 |
| 7,404,809 B2 * | 7/2008 | Susi | 604/131 |
| 7,512,434 B2 * | 3/2009 | Staats et al. | 600/420 |
| 7,751,184 B2 * | 7/2010 | McCoy | 361/679.41 |
| 7,813,118 B2 * | 10/2010 | Burge | 361/679.41 |
| 2002/0072682 A1 * | 6/2002 | Hopman et al. | 600/509 |
| 2002/0130786 A1 * | 9/2002 | Weindorf | 340/815.45 |
| 2002/0134570 A1 * | 9/2002 | Franklin-Lees et al. | 174/58 |
| 2002/0169415 A1 | 11/2002 | Staats et al. | |
| 2003/0050555 A1 * | 3/2003 | Critchlow et al. | 600/420 |
| 2003/0105403 A1 * | 6/2003 | Istvan et al. | 600/509 |
| 2004/0147818 A1 | 7/2004 | Levy et al. | |
| 2004/0230113 A1 | 11/2004 | Bolam et al. | |
| 2005/0107681 A1 | 5/2005 | Griffiths | |
| 2006/0241384 A1 | 10/2006 | Fisher et al. | |
| 2006/0241392 A1 * | 10/2006 | Feinstein et al. | 600/422 |
| 2006/0247512 A1 | 11/2006 | Harwell et al. | |
| 2007/0046837 A1 * | 3/2007 | Elberbaum | 348/739 |
| 2007/0135866 A1 * | 6/2007 | Baker et al. | 607/60 |

FOREIGN PATENT DOCUMENTS

WO  WO 00/64335 A1 * 11/2000

OTHER PUBLICATIONS

NPL_hotshoe.pdf, p. 1-2.*

* cited by examiner

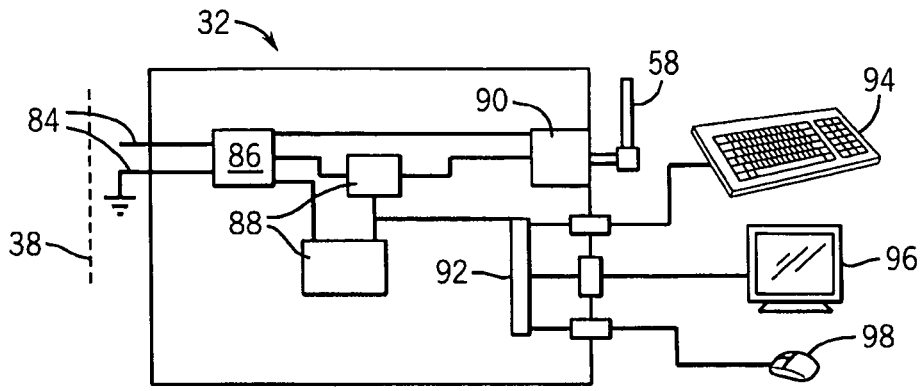
FIG. 5
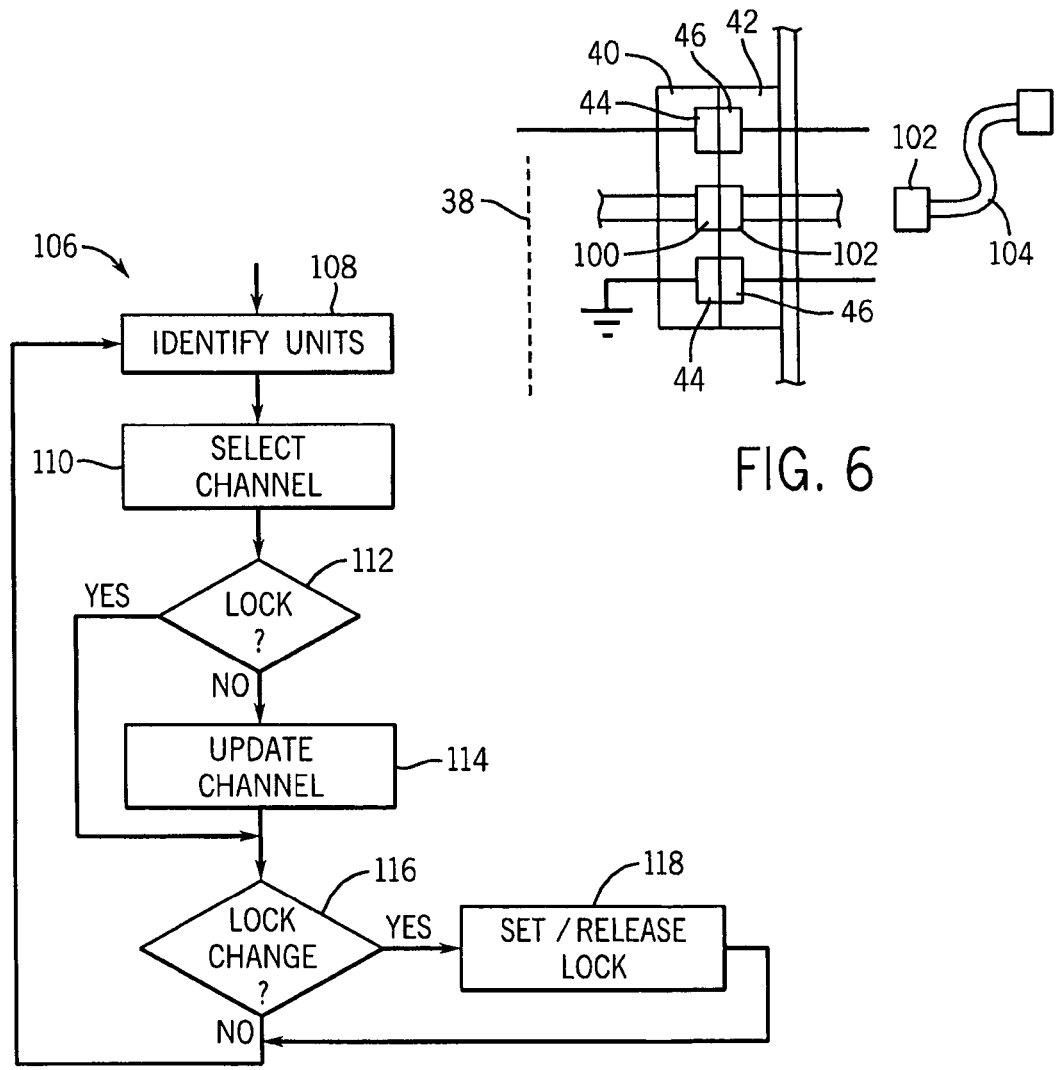
FIG. 6
FIG. 7

INTERFACED BASE UNIT AND DISPLAY SYSTEM FOR AN MRI MAGNET ROOM

CROSS-REFERENCE TO RELATED APPLICATIONS

This application claims the benefit of U.S. Provisional Application 60/799,884, filed May 12, 2006, the disclosure of which is incorporated herein by reference.

STATEMENT REGARDING FEDERALLY SPONSORED RESEARCH OR DEVELOPMENT

Background of the Invention

The present invention relates generally to electronic patient monitors and, in particular, to a detachable display unit suitable for use in the severe electromagnetic environment of a magnetic resonance imaging (MRI) machine.

Magnetic resonance imaging allows images to be created of soft tissue from faint electrical resonance (NMR) signals emitted by nuclei of the tissue. The resonance signals are generated when the tissue is subjected to a strong magnetic field and excited by a radiofrequency pulse.

A patient undergoing an MRI scan may be received into a relatively narrow bore, or cavity, in the MRI magnet. During this time, the patient may be remotely monitored to determine, for example, heartbeat, respiration, temperature and blood oxygen. A typical remote monitoring system provides an "in-bore" patient sensor near the patient connected by electrical or optical cables or by RF data link to a base unit outside of the bore of the MRI magnet.

The base unit customarily includes a display unit that may be consulted before the MRI scan to ensure that the monitoring sensors, for example, ECG leads or blood pressure cuffs are properly positioned and functioning. During the scan, when it is critical that the patient be continuously monitored, one operator may be stationed near the base unit in the MRI room and another will attend to the control of the MRI machine in the control room. The control room is normally separated from the MRI room holding the MRI magnet, and provides consoles and terminals for the MRI machine that allow control of the machine and the display of images from the MRI scan.

Conventional base units are cabled to the patient sensor in the bore of the magnet using optical or electrical cables. Such cable runs can be cumbersome and interfere with access to the patient and free movement of personnel about the magnet itself. This problem is addressed in pending U.S. patent application Ser. Nos. 11/080,958, filed Mar. 15, 2005, and 11/080,743, filed Mar. 15, 2005, assigned to the assignee of the present invention and hereby incorporated by reference, which describe a wireless patient monitor that may be positioned near the patient to provide real-time monitoring of patient physiological signals without cumbersome cables that extend outside of the bore of the magnet.

The inventions described in these applications overcome problems of the electrically noisy environment of the MRI, such as would normally be expected to interfere with radio communications, by using combined diversity techniques including: frequency diversity, antenna location diversity, antenna polarization diversity, and time diversity in the transmitted signals. The quality of the signals is monitored to select among diverse pathways, dynamically allowing low error rates and high bandwidth at practical transmission powers.

Despite these diversity techniques, it may not be practical to transmit wirelessly from within the bore of the magnet into the control room, such as would allow the base unit to be repositioned in the control room itself to be monitored by the operator of the MRI machine. Accordingly, there is a need for a base unit operable in or near the MRI machine during an MRI examination. It would also be desirable to have a display unit detachable from the base unit that would enable an operator to roam with the display unit detached from the base unit, thereby allowing an operator to monitor the display unit remote from the base unit. It would also be desirable to control operation of a wireless patient monitoring system through inputs to the display unit that are wirelessly communicated to the base unit.

SUMMARY OF THE INVENTION

The present invention is generally directed to a base unit having a display that may be detached and used remotely allowing continuous, yet flexible, monitoring of the patient, both near the bore and at other locations without the need for separate displays. The base unit may operate as a repeater to transmit information received from the wireless units in the bore to a remote location where the display is located. The display unit may also operate to transmit information wirelessly to the wireless units in the bore. A magnet-hardened display allows the repositioning of the display at points closer to the magnet bore than would normally be possible with the base unit. In one embodiment, the display unit may be docked to the base unit or other docking stations, such as a wall dock.

Therefore, in accordance with one aspect, the invention includes a base station for an MRI machine having a magnet defining a patient bore. The base station is positionable outside the bore of the magnet during an MRI examination and has a monitor unit that receives wireless transmissions of data from a patient sensor that acquires physiological signals of a patient. The base station further has a display unit that may be positioned remotely from the monitor unit and is capable of wireless communication with the monitor unit to display information associated with the data received from the patient sensor by the monitor unit.

According to another aspect of the present disclosure, a base station for an MRI machine is presented. The base station may be positioned outside or near the magnetic field generated by the MRI machine during an MRI examination. In one embodiment, the base station has a dock, a monitor unit connected to the dock and receives physiological information from a patient during an MRI examination. The base station also has a display unit that may be connected to the dock when desired and configured to wirelessly receive data from the monitor unit during the MRI examination when remote from the dock.

In accordance with another aspect, the present disclosure is directed to a display unit operable to display information acquired from a patient during an MRI examination. The display unit includes a display unit housing enclosing electronic components and having a quick-connect connector for repeated connection to and disconnection from a dock. The display unit also has a screen that displays data associated with information received from the patient during the MRI examination. A battery supplies power to the electronic components and is managed by a magnetically-hardened power supply. The magnetically-hardened power supply is operative in the presence of a high-flux magnetic field, without saturation, during an MRI examination.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 5 is a figure similar to that of FIG. 4 showing the principal components of the base unit, including a computer and a port for the attachment of local displays and keyboard devices;

FIG. 6 is a block diagram of a second embodiment of the hot shoe transmitting, not only electrical power, but also data communication; and FIG. 7 is a flow chart of a program executed by the computer of FIG. 5 of the base unit in coordinating the communications between one or more of the patient sensor, base unit and the remote display.

DETAILED DESCRIPTION OF THE PREFERRED EMBODIMENT

The present invention will be described with the wireless acquisition and transmission of physiological data to a remote display unit that is operative in the magnetic field generated by an MRI magnet. However, it is understood that the present invention may also be useful in other applications involving high-flux magnetic fields.

Figure 1:
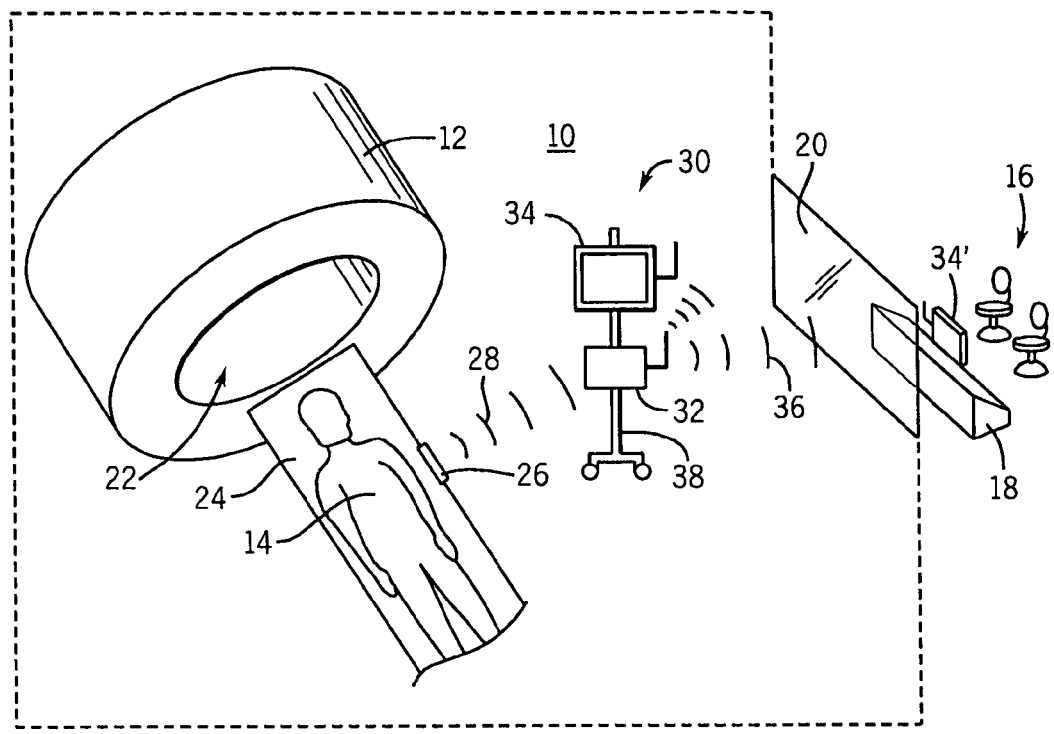
FIG. 1 is a perspective view of an MRI suite showing the MRI magnet with a patient positioned for scanning and connected to a patient sensor, the latter communicating with a base unit positioned within the MRI room away from the bore of the magnet, and further showing a control room outside of the MRI suite shielded from the MRI suite against radiofrequency interference.

Referring now to FIG. 1, a magnet room 10 provides radiofrequency, and possibly magnetic shielding, enclosing an MRI magnet 12. The magnet 12 may be part of an MRI machine controlled from a control room 16 providing a console 18 outside of the magnet room 10 and normally providing a shielded window 20 allowing viewing of the magnet 12 from the control room 16.

A patient 14 may be positioned to be received into a bore 22 of the magnet 12 on a movable table 24 for an MRI scan. Before the scan, a wireless patient sensor or monitor 26 may be connected to the patient 14 to monitor patient physiological signals, including ECG, blood oxygen, blood pressure, and the like.

The patient sensor 26 may communicate via radio waves 28 to a base station 30 positioned outside the bore 22 of the magnet 12 using diversity techniques described in the above referenced co-pending patents hereby incorporated by reference. The base station 30 includes a monitor unit 32 and a display unit 34, both mounted on a stanchion 38, the latter extending upward from an optional wheeled base unit for easy movement. Generally, the monitor unit 32 receives wireless transmissions of data from the patient sensor 26, processes the same, and displays the data (or information associated therewith) on a graphic screen of the display unit 34. The display unit 34 may also include additional processing and user input controls, such as pressure-sensitive switches or a touch screen to provide commands to the monitor unit 32.

In communicating with the display unit, the monitor unit 32 may transmit the data on radio waves 36 implementing a different channel than the radio waves 28 received from the patient sensor(s) 26. In this case, a channel may refer to any combination of logical and physical channel parameters including, for example, frequency, frequency hop patterns, packet identifiers, and the like. Wireless transmission of data to the display unit 34 allows the display unit 34 to be located either on a dock, such as stanchion 38, or remotely located, like display unit 34', for example, on a stanchion or other dock in the control room 16. Alternately, the display unit 34 may be docked on a wall or desk dock in the magnet room 10 or in the control room 16. The control room 16 is normally shielded from the magnet room 10 but may provide a passive or active repeater penetrating the shield and passing radio waves 36 used by the monitor unit 32. The display unit 34 may not only receive physiological data from the base station 30 but may also transmit commands to the base station 30 and, via the base station 30, to the patient sensors 26, for example, as input by an operator. Wireless communication eliminates the problem of cable management and allows the display unit 34 easy, and repeated detachability from the base station 30.

Figure 2:
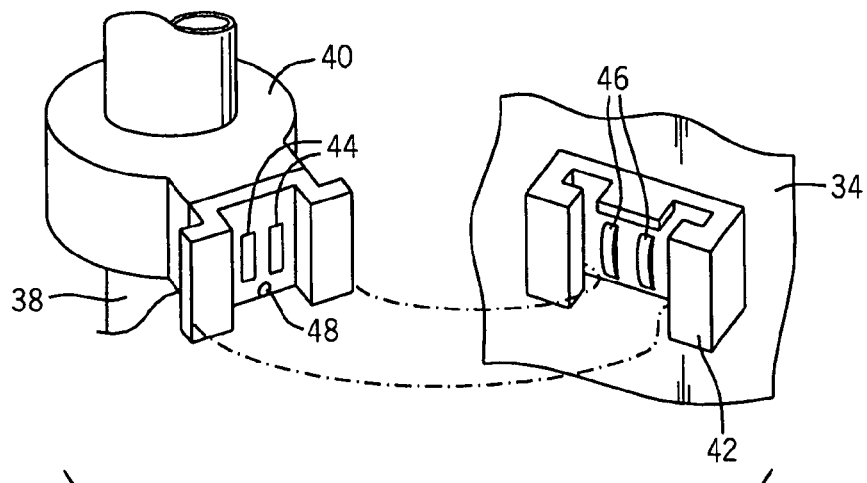
FIG. 2 is a detailed view of a "hot shoe" attached to a pole supporting the display unit, the hot shoe removably holding a display associated with the base unit and providing power to that display.
Figure 3:
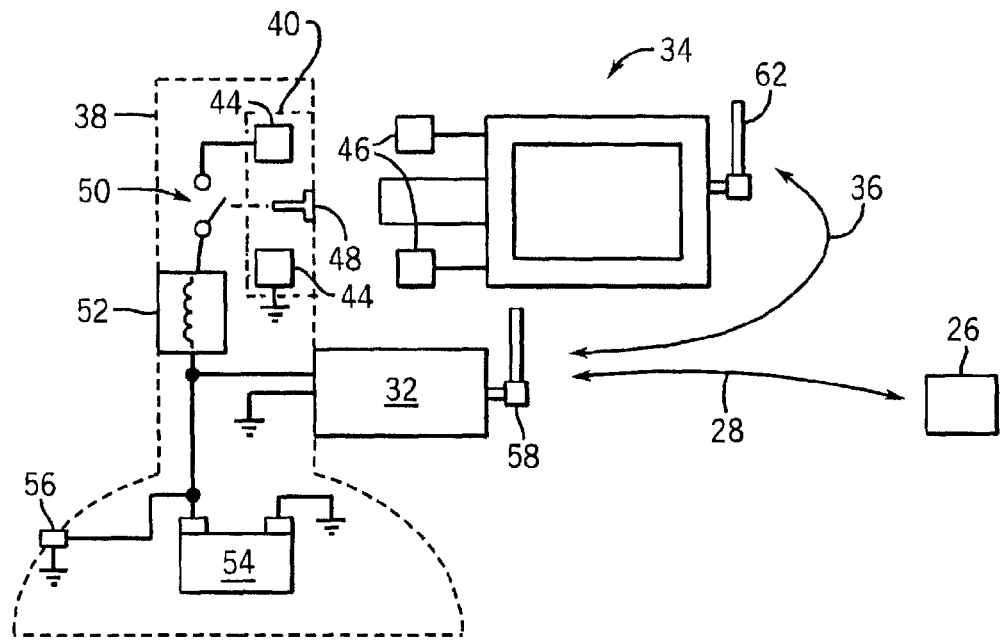
FIG. 3 is a block diagram of the base unit showing electrical connections through the hot shoe between a power supply of the base unit and the display.

Referring now to FIGS. 2 and 3, freedom to relocate the display unit 34 is provided by a hot shoe 40, held by the stanchion 38, which may connect mechanically and electrically with a hot shoe socket 42 mounted on the rear surface of the display unit 34. The hot shoe 40 and the hot shoe socket 42 present a quick-connect connection for attaching or detaching the display unit from stanchion 38. Connecting the hot shoe 40 with the hot shoe socket 42 attaches the display unit 34 to the stanchion 38 or to another remotely located hot shoe (e.g., in the control room 16).

The hot shoe 40 presents a plurality of direct current power contacts 44 that may connect with corresponding contacts 46 in the hot shoe socket 42. When the hot shoe socket 42 is engaged with the hot shoe 40, electrical contact may be had between individual pairs of contacts in 44 and 46. A switch operator 48 may protrude from the hot shoe 40 to be depressed by a surface of the hot shoe socket 42 when the hot shoe socket 42 is engaged with the hot shoe 40. The switch operator 48 closes a switch 50 to connect electrical power and/or ground to the contacts 44 so that power may be provided to the display unit 34 when it is attached to the stanchion 38, but so that power is not exposed on the contacts 44 when the display unit 34 has been removed.

In a preferred embodiment of the invention, the terminal of the switch 50 not connected to one of the contacts 44 is connected to a radiofrequency filter 52 that, in turn, connects to the power side of a storage battery 54 held in the base of the stanchion 38. The filter 52 prevents electromagnetic interference picked up by the wiring of the stanchion 38 from being introduced into the display unit 34 and vice versa.

The monitor unit 32 is also attached to the stanchion 38 and also internally connected to the battery 54. A charge jack 56 is on the base of the stanchion 38 accepting a charger "brick" (not shown) to provide charging current to the battery 54 and operating power to the display unit 34 and monitor unit 32. The display unit 34 also includes an internal battery (as will be described), which may be charged by the charger brick.

The monitor unit 32 includes an antenna 58, which, as described above, allows it to communicate wirelessly with the patient sensor 26 on a first channel formed by radio waves 28 and with the display unit 34 through antenna 62 on a second channel formed by radio waves 36.

Figure 4:
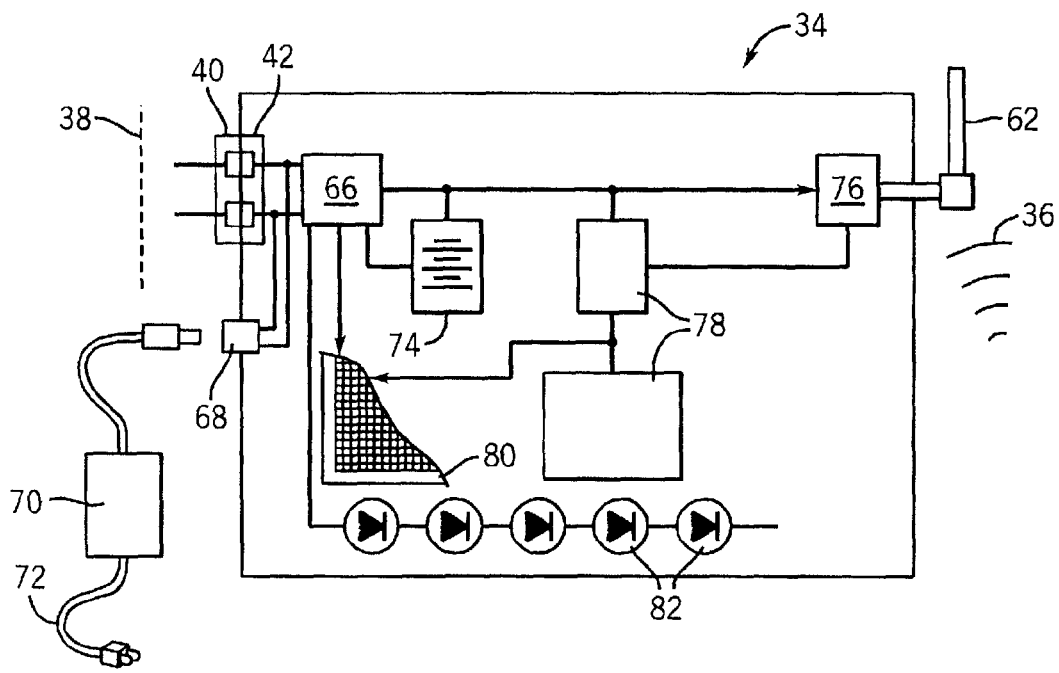
FIG. 4 is a block diagram of the display of FIG. 3, incorporating a magnet-hardened power supply offering several power supply options during local or remote connection.

Referring now to FIG. 4, the display unit 34 receives power through the hot shoe socket 42 at a special magnetically "hardened" power supply 66 in which a standard switching power supply circuit is modified by removal of "soft" ferrite or steel core transformers and replacing them with air core or "hard ferrite" core transformers that may operate without saturation in the environment of the high flux field of the MRI up to approximately 15,000 Gauss. In this way the display unit may operate in magnetic fields of up to 15,000 Gauss in strength.

The power supply 66 may alternatively receive power directly through a charger jack 68 exposed at one side of the display unit 34 that may receive power from a charger brick 70, in turn having a standard line cord 72 for connecting to line power. In addition, charger brick 70 may also supply electrical power to the base station 30 directly through the interconnection of contacts 44 and 46.

When the power supply 66 is receiving power, it, in turn, provides power to a transmitter/receiver 76 connected to the antenna 62 and to control circuitry 78, which may include, for example, a processor, a digital signal processor implemented through discrete circuits or with a field programmable gate array ("FPGA"). The control circuitry 78 may provide signals to a liquid crystal display (LCD) touch screen 80 (or an LCD and switch panel) allowing both the display of data and the acceptance of user commands.

Power supply 66 may also provide power to a string of LEDs 82 allowing for back-lighting of the LCD screen 80 without the need for cold cathode fluorescent tubes and their associated power supplies, which could produce unnecessary interference in the MRI environment and be inoperative in high field environments.

Finally, the switching power supply 66 provides charging power to an internal battery 74 that may be used when the display unit 34 is in a roving mode not connected to the stanchion 38, but communicating with the base unit via the antenna 62. Alternately, or in addition thereof, the display unit may have one or more supercapacitors to provide power to the internal electronic components of the display unit and charged in a known manner using an appropriate charger, when necessary.

Referring now to FIG. 5, the monitor unit 32 may receive power through a direct connection 84 with the stanchion 38 at a power supply 86. Because the stanchion 38 is normally positioned away from the magnet 12 during an MRI examination, the monitor unit 32 may use standard switching power supply components to provide power to processing electronics 88 and transmitter/receiver 90, communicating with antenna 58 to receive information from the patient sensor 26 and to communicate with the display unit 34. The monitor unit 32 may also include a port system 92 providing for communication ports similar to those in a standard personal computer, allowing for the connection of a keyboard 94, a standard display, such as an LCD display 96 and a cursor control device, such as a mouse, 98. This allows the monitor unit 32 to be used independently of connection to the display unit 34.

Referring now to FIG. 6, in an alternative embodiment, the hot shoe 40 may also provide for a data connector 100, in addition to the power contacts 44. Data connector 100 is operationally connected to output data from or input data to the monitor unit 32. Similarly, the hot shoe socket 42 may provide for a corresponding data connector 102 connecting with data connector 100. The data connectors 100 and 102 may, for example, provide for a parallel or serial digital connection of conductors or optical cable or the like, and provide for a path between the monitor unit 32 and the display unit 34 when the display unit 34 is docked on the stanchion 38. When the connectors 100 and 102 are connected, internal software may optionally disconnect the transmitter/receiver 76 in the display unit 34, thereby preventing the generation of unnecessary radiofrequency signals. Similarly, the monitor unit 32 may suppress transmissions from the transmitter/receiver 90 to the display unit 34.

Connectors 100 and 102 allow for the introduction of a jumper cable 104 of arbitrary length allowing a direct cable connection between the monitor unit 32 and display unit 34 for situations where a remote display is required on a semi or permanent basis. By using the jumper cable 104, a remote semi-permanent display may be used in addition to the roving wirelessly-connected display unit 34.

Referring now to FIG. 7 and FIG. 5, the processing electronics 88 may execute a stored program 106 coordinating the wireless communications between the monitor unit 32 and the display unit 34 by properly assigning channels to the communications permitting, for example, the use of multiple display units 34 with one monitor unit 32 or multiple monitor units 32 communicating with one display unit 34 without interference. In order to provide for this unique connection between devices, a channel selection process is employed to logically connect a given monitor unit 32 with a given display unit 34.

As indicated by process block 108, this commissioning process begins with the identification of a particular display unit 34 and monitor unit 32 by the entry of a display identifier or the like, and possibly the entry of a unique serial number or MAC address.

At process block 110, a logical channel or network address is selected for the communication, such as will be provided to both the display unit 34 and monitor unit 32, either manually or by a default communication channel. As before, a channel may refer to any combination of logical and physical channel parameters including, for example, frequency hop patterns, packet identifiers, and the like.

The user may lock the channel selected, preventing inadvertent channel changes, such as may confuse the unique path between a particular patient 14 and a particular display unit 34, such as might permit a user to be misled about the source of particular signals. If the channel is not locked, then, at process block 114, the channel may be changed.

If the channel is locked, then, at decision block 112, the program jumps to decision block 116, which allows the lock state to change per process block 118, possibly requiring a password or the like.

It is specifically intended that the present invention not be limited to the embodiments and illustrations contained herein and the claims should be understood to include modified forms of those embodiments including portions of the embodiments and combinations of elements of different embodiments as come within the scope of the following claims.

What is claimed is:

1. A base station for an MRI compatible patient monitor device, the base station positionable outside a bore of a magnet during an MRI examination, the base station comprising:
 a movable stanchion disposed in a shielded magnetic resonance room;
 a monitor unit which receives wireless transmissions of data from a patient sensor that acquires physiological signals from a patient in the bore of the magnet, the monitor being mounted on the stanchion; and a display unit which wirelessly communicates with the monitor unit and displays information associated with the data received from the patient sensor by the monitor unit, the display unit being movable independently of the monitor unit in the shielded magnetic resonance room, the display init including:

a rechargeable battery that provides power to the display unit when the display unit is remote from the stanchion, the stanchion providing charging current to the rechargeable battery when the display unit is mounted to the stanchion, and a magnetically hardened power supply operative, without saturation, in high-flux magnetic fields up to 15,000 Gauss to manage the rechargeable battery during an MRI examination.

2. The base station of claim 1 wherein the monitor unit receives wireless transmissions of data from the patient sensor on radio waves on a first channel and transmits data to the display unit on radio waves on a second channel different from the first channel.

3. The base station of claim 1 wherein the display unit includes:
an LCD display screen; and
LEDs which backlight the LCD display screen.

4. The base station of claim 1 wherein the display unit includes:
a backlight display screen and backlights which operate in the bore of the magnet and do not interfere with the MRI examination;
a rechargeable battery which powers the backlight display; and
a magnetically hardened power supply which recharges the rechargeable battery without saturation when positioned adjacent to the bore of the magnet.

5. The base station of claim 1 wherein the stanchion carries a first set of contacts and the display device carries a second set of contacts, the first and second sets of contacts communicating to transfer power from the stanchion to the display unit when the display unit is temporarily mounted to the stanchion.

6. The base station of claim 5 wherein the monitor unit automatically suspends wireless communications to the display unit when the display unit is mounted to the stanchion.

7. A base station for an MRI compatible patient monitor device, the base station positionable outside the bore of the magnet during an MRI examination and comprising:
a monitor unit which receives wireless transmissions of data from a patient sensor that acquires physiological signals from a patient;
a display unit positionable remotely from the monitor unit and in wireless communication with the monitor unit to display information associated with the data received from the patient sensor by the monitor unit;
a stanchion, the display unit being mountable to the stanchion when desired, the stanchion having a hot shoe and the display unit having a hot shoe socket which interfaces with the hot shoe when the display unit is mounted to the stanchion, the hot shoe including a first set of contacts and the hot shoe socket including a second set of contacts, the sets of contacts transferring power from the stanchion to the display unit when the display unit is mounted to the stanchion;
the display unit including a rechargeable battery that provides power to the display unit when the display unit is remote from the stanchion, the stanchion providing charging current to the rechargeable battery when the display unit is mounted to the stanchion; and the display unit further including a magnetically hardened power supply to manage the rechargeable battery and being operative, without saturation, during an MRI examination;
wherein the magnetically hardened power supply is operative, without saturation, in high-flux magnetic fields up to 15,000 Gauss.

8. The base station of claim 4 wherein the display unit includes lighting elements which backlight a display screen without interfering with magnetic resonance imaging.

9. The base station of claim 4 wherein the display unit includes light emitting diodes which backlight a display screen without interfering with magnetic resonance imaging.

10. A base station for an MRI compatible patient monitor device, the base station positioned in a radiofrequency shielded magnet room and outside a bore of magnet during and MRI examination and comprising:
a stanchion movably disposed in the radiofrequency shielded magnet room;
a dock mounted on the stanchion;
a monitor unit, connected to the dock, which receives physiological information from a patient in the bore during an MRI examination and processes the received physiological information; and
a display unit connectable to the dock by a quick-connect connector which provides power to the display unit and transfers the processed information from the monitor unit to the display unit when the display unit is connected to the dock, the display unit including a rechargeable battery which powers the display unit when the display unit is disconnected from the dock and a wireless receiver which wirelessly receives the processed information from the monitor unit during the MRI examination when the display unit is disconnected from the dock.

11. The base station of claim 10 wherein the display unit includes a backlight screen and LEDs which backlight the screen when the display is in the bore during the MRI examination without interfering with the MRI examination.

12. The base station of claim 10 wherein the monitor unit is configured to automatically suspend wireless transmission of the processed information to the display unit when the display unit is connected to the dock.

13. The base station of claim 10 wherein the dock includes a hot shoe and the display unit includes a hot shoe socket configured to receive the hot shoe when the display unit is connected to the dock.

14. The base station of claim 13 wherein the hot shoe includes a first set of electrical contacts and the hot shoe socket includes a second set of electrical contacts, and wherein the first and second sets of electrical contacts transfer power from the dock to the display unit when the display unit is connected to the dock.

15. The base station of claim 13 wherein the quick connect connector includes a switch operator that closes a switch when the display unit is connected to the dock to deliver power from the dock to the display unit.

16. The base station of claim 10 wherein the display unit further comprises a magnetically hardened power supply that operates in high-flux magnetic fields up to 15,000 Gauss, without saturation, during the MRI examination.

17. A display unit operable to display information acquired from a patient in a bore of a magnet during an MRI examination, comprising:
a display unit housing enclosing electronic components and having a quick-connect connector for repeated connection to and disconnection from a dock, the electronic components including a receiver for wirelessly receiving data associated with the information received from the patient during an MRI examination;

a screen which graphically displays data associated with information received from a patient during an MRI examination;

a battery;

and a magnetically-hardened power supply that manages the battery to deliver power to the electronic components when the display unit is detached from the dock, and wherein the magnetically-hardened power supply is operative, without saturation, in magnetic fields of up to 15,000 Gauss, during an MRI examination.

18. The display unit of claim 17 further comprising a set of electrical contacts that mate with corresponding electrical contacts of a dock when the display unit housing is connected to the dock, the electrical contacts designed to facilitate the transfer of power from the dock to the at least one of the electronic components and the battery.

19. The display unit of claim 18 wherein the screen is back lit by LED lighting elements which do not interfere with the MRI examination.

* * * * *